United States Patent [19]

Sacks et al.

[11] Patent Number: 5,096,471
[45] Date of Patent: Mar. 17, 1992

[54] GAS CHROMATOGRAPHY SYSTEM AND METHODS

[75] Inventors: Richard Sacks; Christine Rankin; Mark Klemp, all of Ann Arbor, Mich.

[73] Assignee: The Regents of the University of Michigan, Ann Arbor, Mich.

[21] Appl. No.: 590,174

[22] Filed: Sep. 28, 1990

[51] Int. Cl.$^5$ .............................................. B01D 15/08
[52] U.S. Cl. ........................................ 55/67; 55/197; 55/208; 55/386
[58] Field of Search .................... 55/67, 197, 886; 73/23.35, 23.36, 23.41

[56] References Cited

U.S. PATENT DOCUMENTS

| | | | |
|---|---|---|---|
| 3,111,835 | 11/1963 | Jenkins | 73/23 |
| 3,220,164 | 11/1965 | Golay | 55/67 |
| 3,550,428 | 12/1970 | Mator et al. | 73/23.36 |
| 4,271,697 | 6/1981 | Mowery, Jr. | 55/67 X |
| 4,274,967 | 6/1981 | Snyder | 55/67 X |
| 4,477,266 | 10/1984 | Yang et al. | 55/67 |
| 4,536,199 | 8/1985 | Toon | 55/386 X |
| 4,805,441 | 2/1989 | Sides et al. | 55/67 X |
| 4,863,871 | 9/1989 | Munari et al. | 55/386 X |

OTHER PUBLICATIONS

"Sample Enrichment in High Speed Narrow Bore Capillary Gas Chromatography", van Es et al., J. of High Resolution Chromatography & Chromatography Communications, vol. 11, 12/1988, pp. 852-857.
"Rapid Evaporation of Condensed Gas Chromatographic Fractions", Hopkins et al., J. of Chromatography, 158 (1978) 465-469.
B. A. Ewels and R. D. Sacks, 1985, Electrically Heated Cold Trap Inlet System for High—Speed Gas Chromatography.
Lanning, Sacks, Mouradian, Levine, Foulke, Electrically Heated Cold Trap Inlet System for Computer—Controlled Controlled High—Speed Gas Chromatography.
S. Levine, R. Sacks, 7/1/86-6/30/88, Fast—GC for Industrial Hygiene Monitoring/Analysis.

Primary Examiner—Robert Spitzer
Attorney, Agent, or Firm—Harness, Dickey & Pierce

[57] ABSTRACT

Gas chromatography apparatus and procedures are described which enables gas chromatography to be carried out more rapidly than in accordance with prior art techniques and further enables chromatogram peaks caused by materials of interest from being obscured due to their super imposition upon high peak long durations produced by another component of peaks in an organic mixture. Reductions in chromatography evaluation time are achieved through employing a vacuum pump which caused backflushing of a very short column after materials of interest have been eluted but before higher boiling points components of the mixture have eluted. Backflushing is carried out using a vacuum pressure source which when used with a short column, permits rapid and complete backflushing. The chromatography system according to this invention allows simultaneous column backflushing while a new sample is being collected in a cooling chamber for cryofocussing for a subsequent injection. Another aspect of the invention is to cause a reversal in the flow direction through the column to occur at or just after a high intensity long duration peak causing component the mixture has eluted causing the remaining components to be drawn back into a thermal focusing chamber for subsequent injection. By stopping the process at this point the concentration of high long duration peak forming materials which have been eluted can be reduced so that subsequent reinjection will reveal features of interest in the chromatogram which would have otherwise been obscured.

13 Claims, 7 Drawing Sheets

GAS CHROMATOGRAPHY SYSTEM AND METHODS

BACKGROUND AND SUMMARY OF THE INVENTION

This invention relates to a gas chromatography system and methods for increasing the speed, operational flexibility, and accuracy of gas chromatography procedures.

Gas chromatography is a widely employed technique for the separation and analysis of complex mixtures of volatile organic and inorganic compounds. The mixture is separated into its components by eluting them from a column having a sorbent by means of moving gas.

Gas chromatography procedures can be classified into two major divisions; gas-liquid chromatography and gas-solid chromatography. Gas-liquid chromatography is presently the most widely employed type and incorporates a nonvolatile liquid sorbent coated as a thin layer on an inert support structure, generally a capillary tube. The moving gas phase called the carrier gas flows through the chromatrographic column. The analyte partitions or divides itself between the moving gas phase and the sorbent and moves through the column at a rate dependent upon the partition coefficient or solubility of the analyte components. Various types of columns are employed such as tubular glass or stainless steel capillary tubes. In use, the analyte is introduced at the entrance end of the column within the moving carrier gas stream. The components making up the sample become separated along the column and escape from the exit end of the column at intervals and in concentrations characteristic of the properties of the analyte components. A detector, for example, a thermal conductivity detector or a flame ionization detector (FID) at the exit end of the column responds to the presence of analyte components. Upon combustion of the eluted material in the FID, charged species are formed in the flame. The flame behavior is monitored through a biased ion detector which, along with associated electronics, produces a time versus magnitude trace of the detector output. The trace for a complex mixture includes numerous peaks of varying intensity. Since individual constituents of the analyte produce peaks at characteristic times and whose magnitude is a function of their concentration, much information is gained through an evaluation of the chromatogram.

Gas chromatography systems of the type described above are in wide-spread use today. Although present systems provide excellent performance and utility, this invention seeks to optimize and further enhance the usefulness of the procedure.

Present gas chromatography apparatus and techniques often require significant analysis times necessary to complete the analysis of a single sample. Such time requirements are imposed due to several factors. The use of long columns (i.e. greater than 10 m) increases the time necessary for materials of interest to traverse the entire column. Long column lengths are traditionally necessary since the sample cannot be delivered at the entrance end of the column as a highly concentrated plug of material but rather is introduced over a significant time period. In order to provide acceptable definition in the separated mixture when the sample cannot be introduced as a dense plug, it is necessary to allow the analyte to travel significant distances along the separation column to avoid smearing of the output caused by differences in the time that portions of the analyte are introduced into the column. In addition, for some analytes the process of complete separation is significantly increased due to the presence of relativity high boiling point components which travel very slowly along the separation column. Although all of the significant information desired from the procedure might be obtained within a relatively short time period as the peaks of interest are generated in the chromatogram, it is necessary to wait for these higher boiling point components to be eluted from the column until the next sample can be introduced.

A further time constraint in traditional gas chromatography procedures is the backflushing process. Following separation, it is ordinarily necessary to backflush the column by providing a fluid stream which travels in a direction opposite that which the analyte moves during separation. This process cleanses the column of any analyte components which might remain and enables the column to be used a greater number of cycles. Since the time for backflushing necessary to purge the column is a function of the square of its length, long column gas chromatography systems require a significant time in which to conduct a gas chromatography experiment.

The above mentioned time constraint on conducting gas chromatography evaluations using traditional systems can limit its utility in applications such as process control procedures or gathering large samples of data in order to provide statistical process quality assurance information.

The gas chromatography system and procedures in accordance with the present invention achieve significant reductions in the time necessary to conduct a gas chromatography evaluation. These improvements in evaluation time are attributable to a number of factors. First, the gas chromatograph in accordance with the present invention utilizes a column of relatively short length i.e. less than 10 meters and preferably about 2 meters. In addition, a cryofocussing chamber is used which causes the sample to be trapped in a solid phase and is then vaporized using a novel rapid heating circuit, enabling the sample to be injected into the inlet end of the column as a high density narrow plug. This concentrated sample plug provides acceptable resolution while using a short column.

This invention further reduces analysis time through incorporating a backflush system in which a vacuum pump is used to reverse the flow direction of fluid through the column after the low boiling point components (relative to other components) of the mixture which are of interest have eluted from the column. Accordingly, high boiling point materials which have not traveled a long distance along the column can be vented through backflushing in a comparatively short period of time. This backflushing operation is achieved using a vacuum pump which draws the fluid through the separation column in a reverse direction without requiring the use of compressed gas sources to drive the backflushing flow, which are necessary when using long columns.

Another area for optimization of gas chromatography evaluation provided by this invention relates to the fact that some samples produce chromatograms having a high intensity broadened peak having a long "tail" generally caused by a solvent in the mixture, and hence is referred to as a "solvent peak". Impurity substances which may elute along the solvent peak or along the solvent peak tail may become completely obscured due to their relatively short time duration and small magnitude as compared to that of the solvent peak. Accordingly, significant data can be obscured.

Systems are presently known for avoiding the problem of data obscuration caused by the presence of solvents mentioned above. For example, so-called heart cutting procedures using multiple columns have been used. However, these procedures significantly complicate the gas chromatography equipment needed, require more control inputs, and significantly increase the time necessary to complete the evaluation.

In accordance with the present invention, a gas chromatography system is provided with means for controlling flow direction through the system element which allows the flow direction through the column to be reversed just at the point where the high concentration solvent components have eluted, but before components of interest following the solvent peak have eluted from the column. These components of interest are returned through the column in a reverse direction and into the cryofocussing device where they are refocused by cooling and subsequently rapidly heated and reinjected into the column. Since these materials are free from at least some of the high concentration material causing the solvent peak the presence of other components of interest are more readily detected upon a second separation process. This process of flow reversal and sample recollection (referred to later as "backflush and retrap" mode) in order to eliminate significant amounts of solvent can be repeated numerous times to provide near complete removal of the solvent materials or materials creating high magnitude, long duration peaks.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
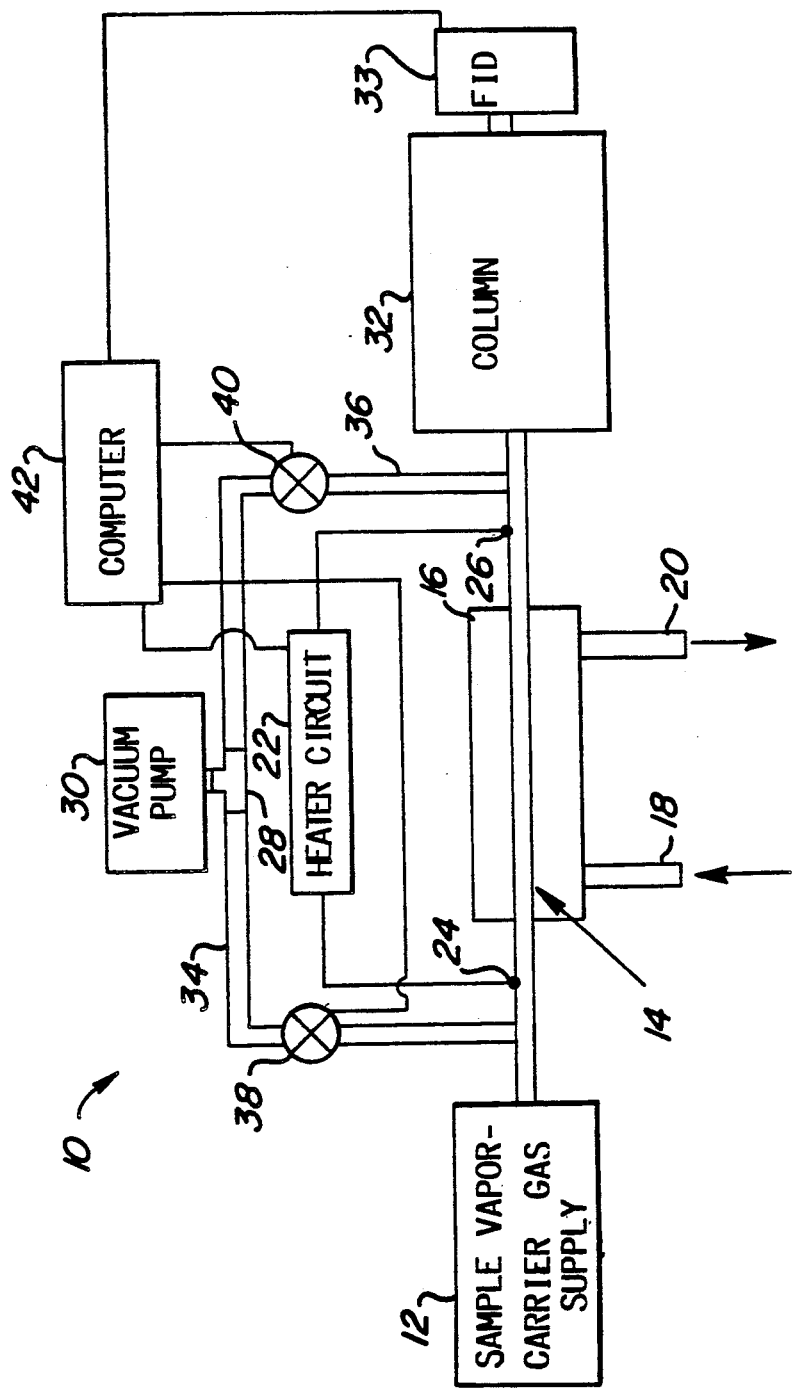
FIG. 1 is a pictorial view of a gas chromatography system in accordance with this invention.

FIG. 1 provides a pictorial view of the basic arrangement of the gas chromatography system according to this invention, which is generally designated by reference number 10. As shown in the figure, this system includes a sample vapor and carrier gas supply 12 which provides a means of introducing an analyte sample and also acts as a supply of a carrier gas such as nitrogen or hydrogen or helium. Supply 12 is in fluid communication with an elongated metal capillary tube 14 which is disposed within cooling chamber 16 having gas inlet and outlet connections 18 and 20, respectively. Gas connections 18 and 20 permit a cold gas such as nitrogen to flow through the cooling chamber to cause extreme cooling of metal capillary tube 14 and the contents within the hollow core of the tube. Cooling chamber 16 is used for cooling capillary tube 14 for thermal focusing which is a process for producing small compact plugs of analyte for gas chromatography evaluation. Heater circuit 22 is shown connected to metal capillary tube 14 at junctions 24 and 26. Heater circuit 22 preferably incorporates a capacitive discharge (CD) power supply which allows a relatively high current spike to be passed through metal capillary tube 14 between junctions 24 and 26, causing extremely rapid heating of the capillary tube. Temperature rise rates of 100,000° C./sec have been produced through such a heater circuit 22. As will further be described, such heating causes vaporization of the sample to create an analyte "plug" for injection into chromatography column 32.

Figure 7:
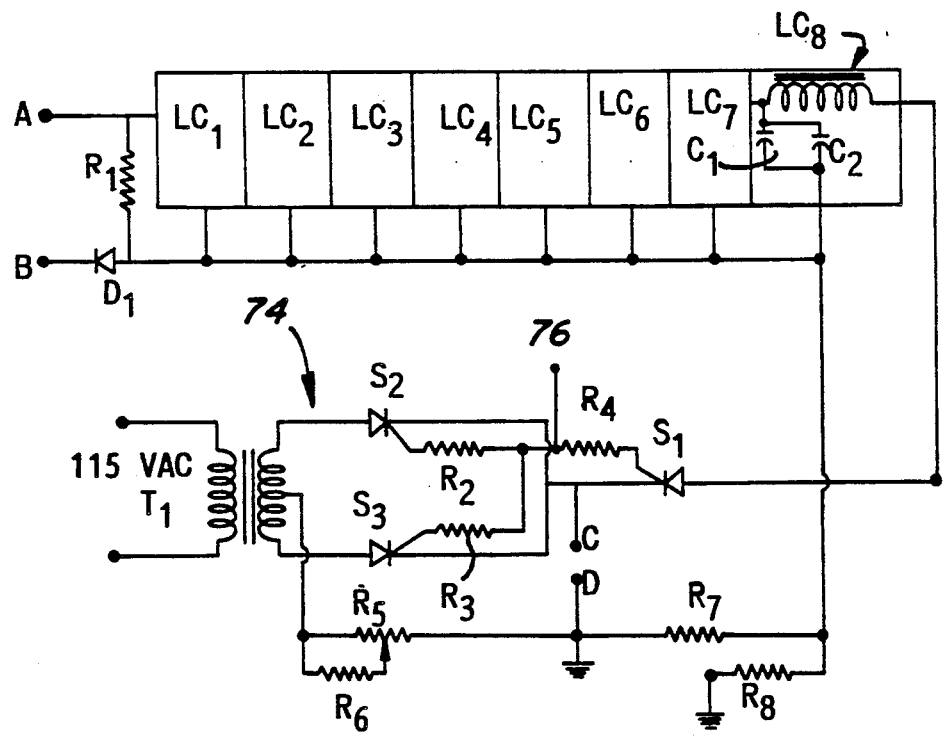
FIG. 7 is an electrical schematic diagram of the capacitive discharge heater circuit according to this invention.

The details of heater circuit 22 are shown in FIG. 7. Each of the LC circuits $LC_1$-$LC_8$ comprises a pair of capacitors of about 1000 micro F arranged in parallel, with each pair of parallel coupled capacitors $C_1$ and $C_2$ coupled in series with an inductor L of 107MH. LCl through $LC_7$ are identical to $LC_8$ which is shown in detail. A DC voltage of about 10-100 volts is applied across charging input terminals A and B, to thereby charge the capacitors $C_1$ and $C_2$ in each of the LC circuits $LC_1$-$LC_8$. Diode $D_1$ has been provided to provide input protection to the power supply. Resistor $R_1$ has been included to help limit the current drawn from the power supply when the supply is initially switched on and the LC circuits $LC_1$-$LC_8$ are charged from a completely uncharged state. Resistor $R_8$ is provided between $C_2$ and electrical ground.

The circuit of FIG. 7 further includes discharge control subcircuit 74 to controllably enable discharging of each of the capacitor pairs within each LC circuit $LC_1$-$LC_8$. The discharge control circuit 74 includes a center tapped transformer $T_1$, and three SCR's $S_1$, $S_2$ and $S_3$. A positive, switchable trigger voltage applied at 76 causes each of the SCR's $S_1$-$S_3$ to go from a normally reversed biased (i.e., open) state into a conducting state and a resistor $R_7$ is provided for monitoring the discharge voltage. The load which is metal capillary tube 14 is connected at terminals C and D.

In operation, $LC_1$–$LC_8$ are charged by the voltage across charging input terminals A and B and held in a charged state by normally reversed biased $S_1$. When a high current pulse is needed across the load terminals C and D, the positive trigger voltage is applied (i.e., switched on) at 76, thus causing SCR's $S_1$, $S_2$ and $S_3$ to each become forward biased. This enables the capacitor pairs within each of the LC circuits $LC_1$–$LC_8$ to discharge through each of their respective inductors $L_1$ through $L_8$, and through the load connected between load terminals C and D. While discharging is taking place, current generated by transformer $T_1$ is allowed to flow through forward biased SCR's $S_2$ and $S_3$ and also through the load. The current flow through SCR's $S_2$ and $S_3$ represents a very small "sustaining" current which can be allowed to flow through the capillary tube 14 even after complete discharging of the capacitors within the LC circuits has occurred. This is accomplished by simply holding the trigger voltage on for a short period of time, for example, 50 milliseconds, after complete discharging of the capacitors within the LC circuits has occurred. Thus, by using the trigger voltage applied at 76, discharging of the capacitors $C_1$ and $C_2$ within the LC circuits can be controlled, as well as the application (and duration of application) of a small sustaining current supplied by transformer $T_1$. The inductor L in each of the LC circuits $LC_1$–$LC_8$ simply serves as a timing device to help time the discharge of the capacitors within its associated circuit.

Resistor $R_7$, it will be appreciated, will indicate the same potential as that being applied to charging input terminals A and B. Accordingly, when discharging occurs it can be monitored by monitoring the potential difference across R7 Resistors $R_5$ and $R_6$ provide a means for adjusting the sustaining current. $R_2$, $R_3$ and $R_4$ are used to control current applied to the triggers of $S_2$, $S_3$ and $S_1$, respectively.

In accordance with the principal feature of this invention, gas chromatography system 10 incorporates vacuum pump 30 for purposes of controlling the direction of fluid flow through the chromatography column 32 and capillary tube 14. Through a tee connection, 28 vacuum pump 30 is connected to capillary tube 14 between sample and vapor supply 12 and cooling chamber 16 via conduit 34. Similarly, conduit 36 communicates vacuum pump 30 to capillary tube 14 at a point between cooling chamber 16 and column 32. Valve assemblies 38 and 40 are provided to either stop or permit the flow of fluid through conduits 34 and 36, respectively. Valve assemblies 38 and 40 each include a solenoid valve operated pneumatic valve which receives control signals from computer 42. When energized, the solenoid valve opens to allow a pressurized gas source (e.g. air) to flow to a micro-pneumatic control valve. These inventors have employed successfully for this application an on-off micro-pneumatic valve made by Scientific Glass Engineering identified as model no. A8683.

Column 32 shown diagrammatically in FIG. 1 is comprised of a relatively short separation column which, in preferred embodiments of this invention, would be approximately two meters in length but in any case is less than ten meters in length. These inventors have used columns made of fused silica glass having a 0.25 mm i.d. Column 32 is placed within a temperature control chamber (not shown) so that the separation temperature can be precisely controlled as it strongly affects separation behavior of the sample. The detector unit 33 can be comprised of various types of detector 33, however, a flame ionization detector (FID) is preferred. FIG. 1 further illustrates the use of computer 42 which controls the operation of valve assemblies 38 and 40, heater circuit 22 and receives the output from detector 3 for analysis.

The basic operation of gas chromatography system 10 proceeds by initially having valve assemblies 38 and 40 in a closed position. A carrier gas, for example, hydrogen is caused to flow through capillary tube 14. This gas flow passes through metalcapillary 14 and through column 32 and detector 33. The sample in vaporized form is mixed into the carrier gas. Cooling chamber 16 is cooled by causing a cryogenic fluid to flow through ports 18 and 20. The metal capillary tube 14 within chamber 16 is typically coiled to provide a relatively high surface area exposed to cold environment in cooling chamber 16. The analyte becomes frozen within the tube 14 and, adheres to the inside surfaces of tube 14. Such operation is often referred to as "thermal focusing". After a sample collection interval of for example, two seconds, metal capillary tube 14 is rapidly heated by a current pulse from heater circuit 22 which incorporates a capacitive discharge energy storage circuit for providing a low voltage short duration spike. The voltage spike from heater circuit 22 is capable of increasing the temperature of metal capillary tube 14 at a rate of about 100,000° C. per second. This heating results in rapid revaporization of the sample creating a sample vapor plug which is then directed by the carrier gas flow to be injected into capillary column 32 for gas chromatographic separation. The extremely high heating rate of capillary tube 14 provided by capacitive discharge heater circuit 22 causes the sample to be injected at the inlet end of column 32 in the form of a very narrow plug which enhances the resolution of the output. For relatively small samples, the injection band width may be in the 5–10 ms. range.

Figure 2A:
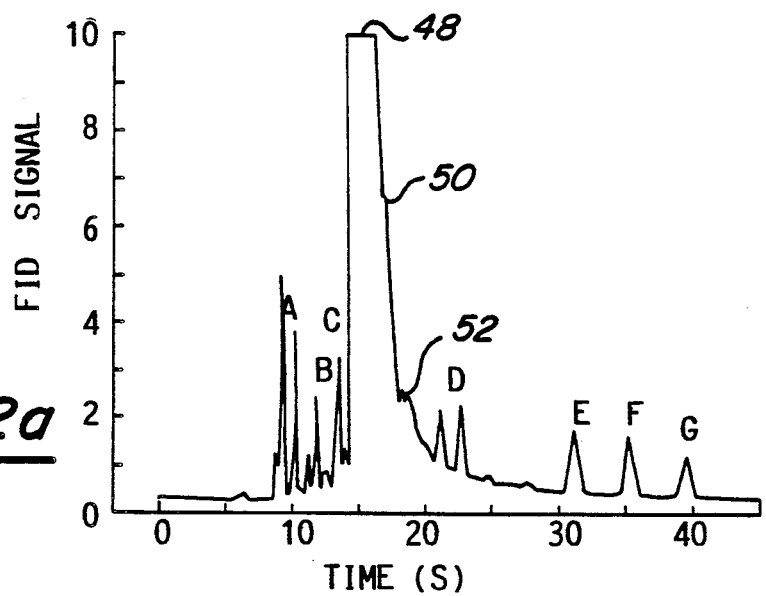
FIGS. 2(a) through 2(c) are a series of chromatograms showing in FIG. 2(a) a complete chromatogram of a material without flow direction reversal, in FIG. 2(b) a chromatogram after a backflush mode is initiated, and in FIG. 2(c), a chromatogram for reinjecting the residue after it has been collected in a cryofocussing trap.
Figure 2B:
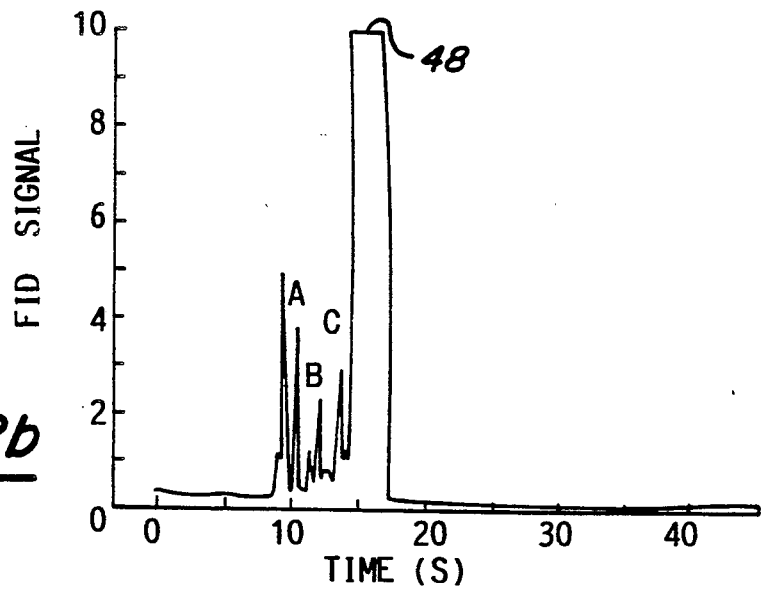

Now with reference to FIG. 2, the operation of a conventional system is described together with the operational capabilities of chromatography device 10 are shown to illustrate one of the operating modes of this invention. The chromatogram shown in FIG. 2(a) is an example chromatogram resulting from a 6.0-nanoliter initial injection of high purity iso-octane spiked with pentane (A), hexane (B), benzene (C), n-octane (D), p-xylene (E), o-xylene (F) and nonane (G) which produce the peaks identified by the corresponding letter designator. The material was first cryofocussed in cooling chamber 16 to a temperature of about −60° C. The traces for FIG. 2 also represent the use of a 4.0 meter column with an average carrier gas flow velocity of about 70 cm/s using $H_2$. As shown in FIG. 2(a) a very dominate solvent peak is shown and identified by reference number 48. Several of the spiked impurity peaks identified by letters A through G are observed on the tail or down slope of the solvent peak 48. As will be evident from the following discussion, solvent peak 48 is superimposed upon other peaks of interest and has largely obscured them due to their relatively small intensity and duration as compared with that of the solvent peak.

In accordance with a principal aspect of this invention an operation referred to as "backflush and retrap" is provided, and through it the significant obscured peaks are recovered through precisely controlling the flow direction of the fluids through column 32 and metal capillary tube 14. Through opening valve assembly 38 while vacuum pump 30 is operating, a backflushing mode can be initiated after the sample is injected into column 32, in which the carrier gas flow direction through capillary tube 14 as it passes through cooling chambers 16 and column 32 is reversed. In chromatogram 2(b) the output of the detector is shown when the flow direction is reversed at 17.0 seconds after the sample was injected into column 32. The detector signal falls rapidly toward zero as the flow direction is reversed. Since the peaks which are observed in FIG. 2(b) identified as peaks A,B,C and 48 resulted from components which have eluted from the column, these separated elements are removed from the remaining components which produce peaks D,E,F,G shown in FIG. 2(a). These materials which have not eluted from column 32 at the 17.0 second point are drawn in a reverse direction through the column and into cooling chamber 16. At this point, current flow provided by heater circuit 22 is no longer flowing allowing capillary tube 14 to be cooled cryogentically by the cold fluid within cooling chamber 16.

Figure 2C:
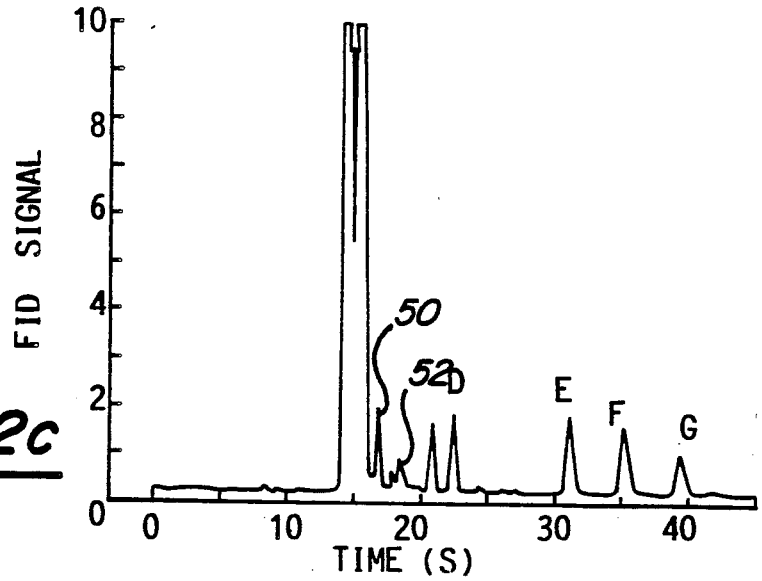

Since the flow direction is in a reverse sense from right-to-left through cooling chamber 16, the remaining constituents of the analyte become retrapped for refocusing in cooling chamber 16. Following this flow reversal for a period of, for example, five seconds, valve 38 can again be closed allowing normal left-to-right flow direction for the carrier gas to occur. Thereafter, another current pulse is produced by heater circuit 22 to revaporize the remaining analyte components. Since a large quantity of the solvent has been eliminated from the collected mixture, peaks of interest appear as shown in FIG. 2(c) which were previously unnoticed or obscured. In particular, peaks 50 and 52 are apparent in FIG. 2(c) which were largely buried in FIG. 2(a). By again inspecting FIG. 2(a), the presence of peaks 50 and 52 can be noticed, although they are largely obscured. In particular, peak 50 appears as a small shoulder on the solvent peak and is virtually undetected in FIG. 2(a). Therefore, this mode of operation allows mixture components which appear on or near solvent peaks to be evaluated in the same manner as components which tend to elute in a discrete fashion.

Although the backflush and retrap procedure of this invention involve the change in fluid flow direction, it does not adversely affect analysis time significantly when used with relatively short columns, for example two meter length columns.

Figure 3:
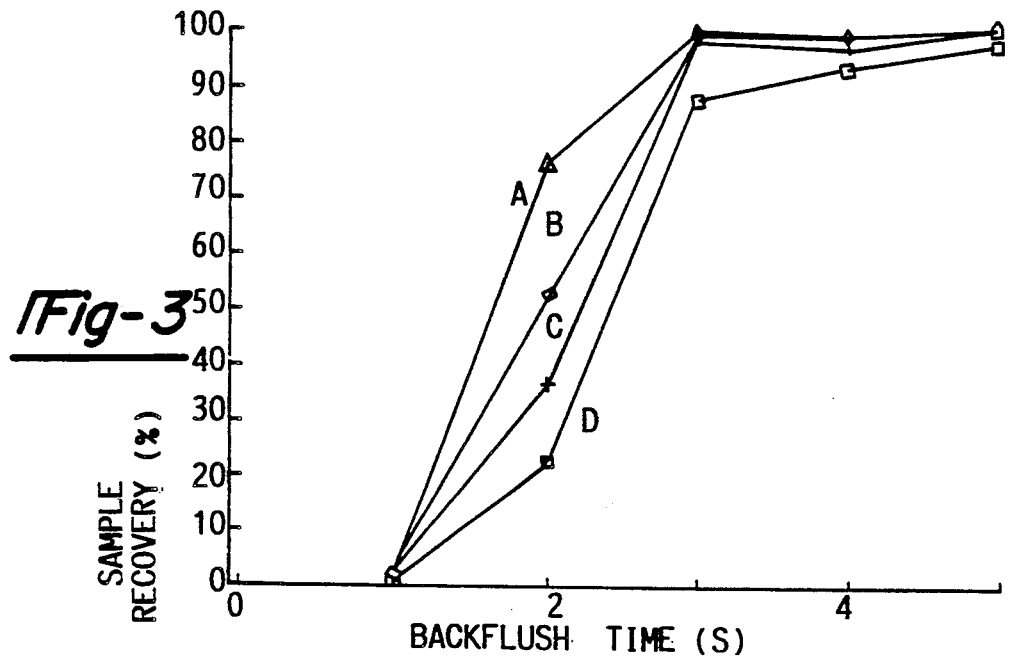
FIG. 3 shows the relationship between various solvent types showing sample recovery efficiency versus various backflush times.

FIG. 3 represents the relationship between various solvent types including nonane (A), o-xylene (B), p-xylene (C) and octane (D) showing the sample recovery efficiency versus various backflush times. As is shown, a backflush time of five seconds assures an extremely high sample recovery percentage for each of the analytes evaluated. In fact for some materials such as nonane (A), a backflush time of only two seconds is sufficient to collect over 75 percent of the material. Since for vacuum operated backflush systems, the minimum backflush time scales as a square of a column length, the use of a short column in accordance with this invention of around two meters provides significant benefits.

The series of chromatograms shown in FIG. 4 represent the output provided by the system 10 in accordance with the time at which backflushing is initiated in the backflush and retrap mode of operation. The traces of FIG. 4(a)–(d) illustrate several solvent flush backflush, retrap and reinjecting sequences for 0.1 nL injections of 0.20 percent o-xylene in HPLC-grade p-xylene. A 2.0 meter long column was used to produce these figures and with a carrier gas velocity of 100 cm per second. Chromatograms 4(a), (b), and (c) and (d) are for backflush initiation times of 9.10s, 9.30s, 9.50s and 9.70s, respectively, after the initiation of injection. These times for backflush initiation are more easily discerned through their designation by the vertical arrows in the expanded time inset of FIG. 4(e). FIG. 4(e) also shows the o-xylene peak 54 on the solvent tail in the case where there is no backflushing operation. For each backflush time shown in FIGS. 4(a) through 4(d), two chromatograms are shown. The left hand chromatogram was obtained during the solvent flush as detected by FID 33. The steep trailing edge of the FID signals in FIGS. 4(a) through 4(d) corresponds to the time at which reversal of the gas flow direction occurred. The four chromatograms on the right side of FIGS. 4(a) through 4(d) were obtained by reinjecting the residue which had been recryofocused during a backflush interval of 5.0s. The size of the residual solvent peak decreases rapidly with increasing backflush initiation time due to an enhanced rejection of the solvent.

Figure 4A:
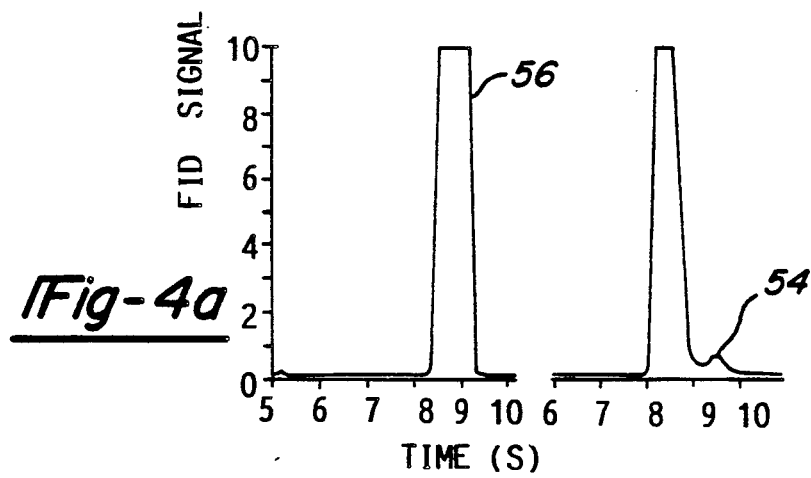
FIGS. 4(a) through 4(f) show, in FIGS. 4(a) through 4(d) a series of chromatograms showing the initial and reinjections characteristics for various backflush times, and in FIG. 4(e), a chromatogram on an expanded time scale illustrating the backflush times of FIGS. 4(a) through 4(d), and at FIG. 4(d) an enlarged and overlayed chromatogram of a peak of interest.
Figure 4B:
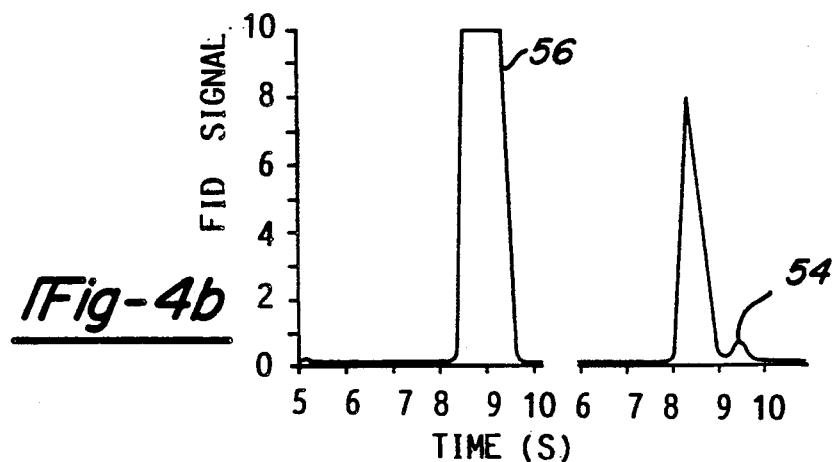
Figure 4C:
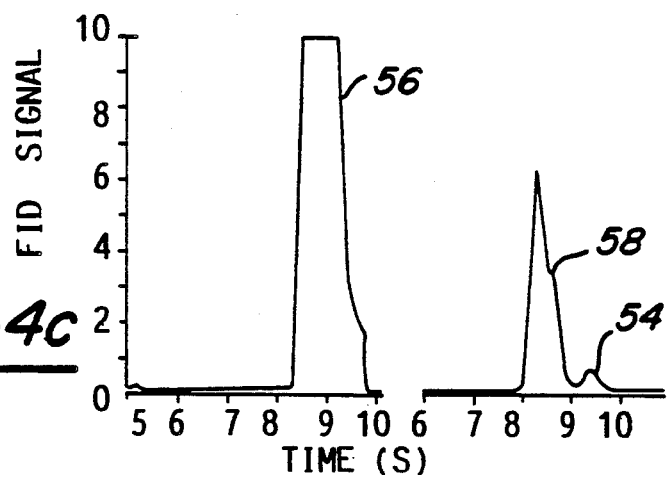
Figure 4D:
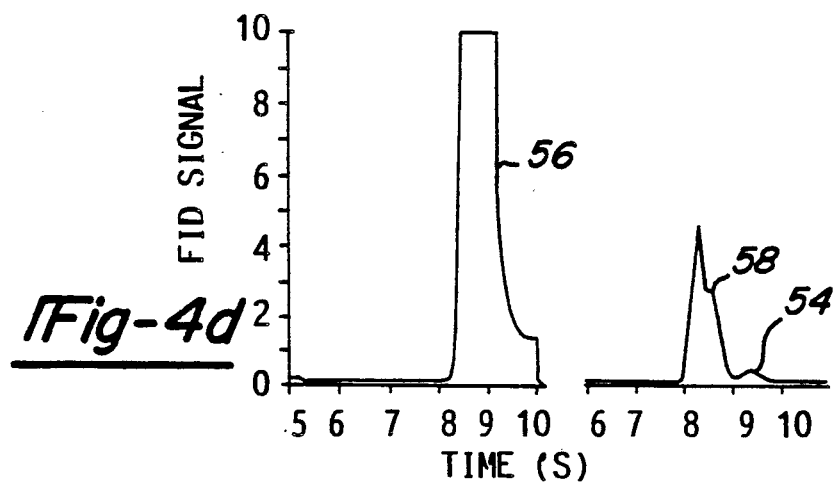
Figure 4E:
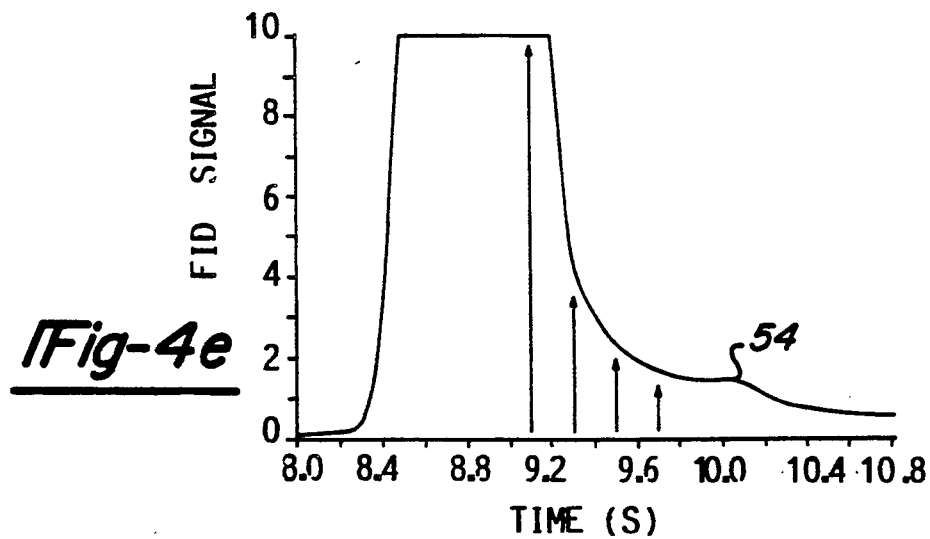
Figure 4F:
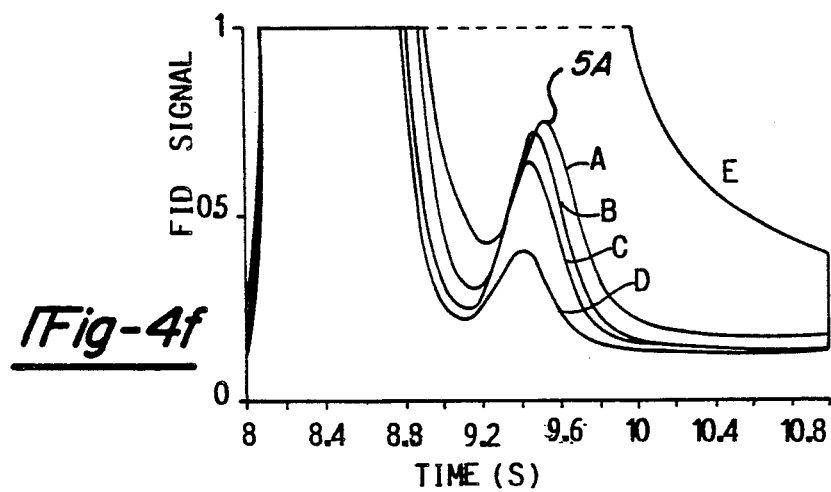

FIG. 4(f) provides a detailed comparison of the region near the p-xylene peak identified by reference number 56 for the four backflush time corresponding with FIGS. 4(a) through 4 (d). The much broader peak E is for a case with no backflush. It should be noted that the o-xylene peak 54 in FIG. 4(f) curve E is completely obscured due to the broad solvent peak that it is superimposed upon. Also evident from the figures is the m-xylene peak 58 which becomes evident with greater backflush times shown in FIGS. 4(c) and (d) since these greater backflush times correspond to enhanced solvent rejection. FIG. 4(f) also illustrates that delaying backflushing times results in a greater removal of the solvent and its associated tail and thus the peak 56 shown in the FIG. 4(f) for case D exhibits a relatively small solvent tail effect.

Figure 5A:
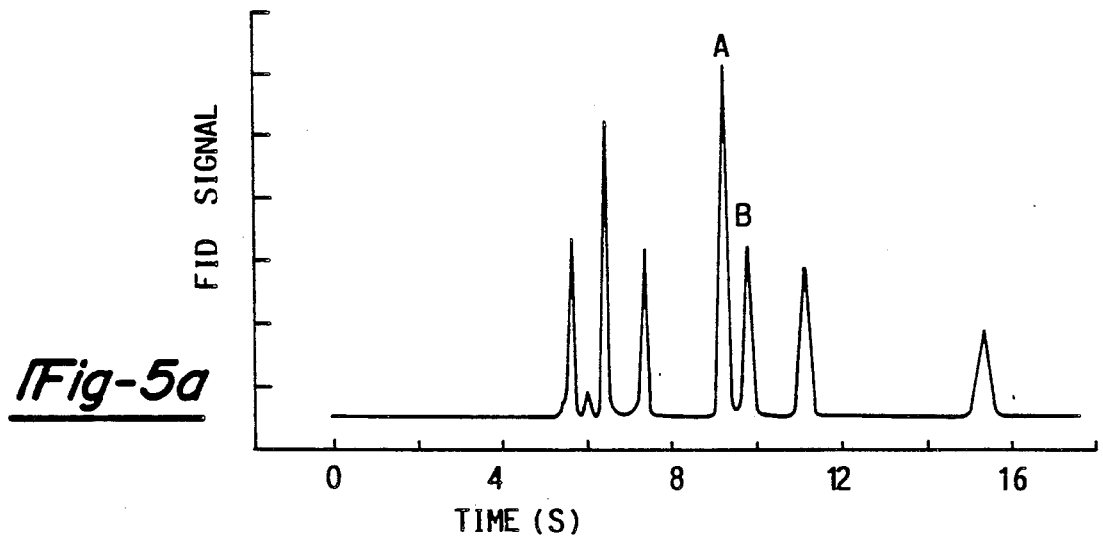
FIGS. 5(a) through 5(c) show, in FIG. 5(a), a complete chromatogram of a mixture of interest, in FIG. 5(b), a partial chromatogram of a solvent and a small quantity of a component of interest, and at FIG. 5(c), a partial, enlarged chromatogram for various numbers of backflush cycles.
Figure 5B:
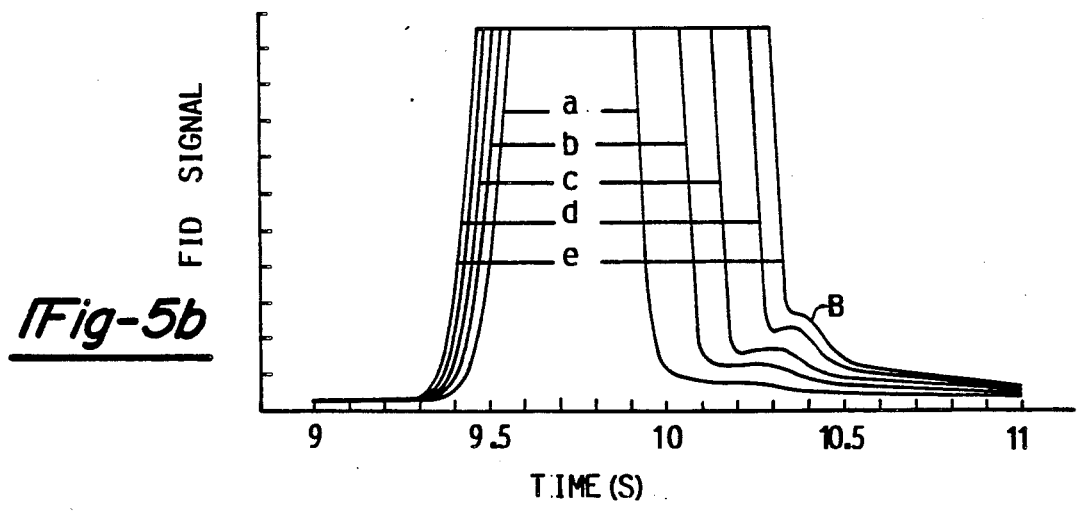
Figure 5C:
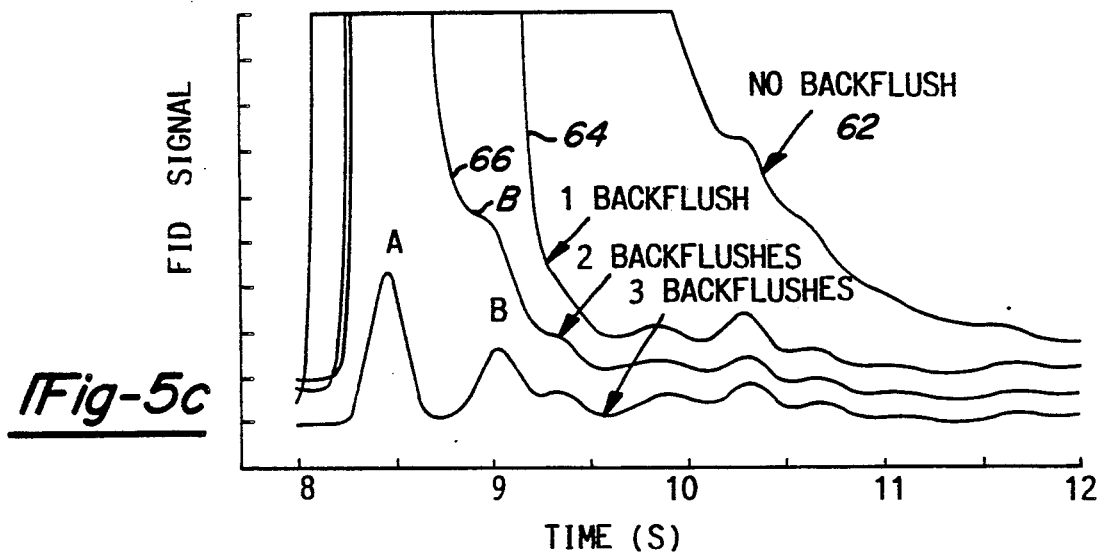

In accordance with the present invention, it is further possible to cause the system to produce multiple backflushes for continued enhancements in the degree of rejection of solvents or other large peak producing components within an analyte. FIG. 5(a) provides a chromatogram showing a mixture containing toluene peak A and 2-fluorotoluene peak B as well as additional compounds. For this chromatogram about 0.04 nL of each component was present. The chromatogram of FIG. 5(b) shows, on an expanded time scale, the effects of sample size on a mixture containing only 0.2 percent 2-fluorotoluene in toluene. The traces in FIG. 5(b), labeled a,b,c,d, and e correspond to sample volumes of 5.7 nL, 11.4 nL, 17.1 nL, 22.8 nL, and 28.5 nL, respectively. In FIGS. 5(b) the 2-fluorotoluene peak B appears as a small shoulder on the tail of the significantly broadened toluene peak A. As will be shown, despite this vast difference in concentration, it will be possible to virtually eliminate the effects of the large toluene peak A through repeated backflushing operations. As evident from FIGS. 5(b), as sample size increases from 5.7 to 22.8 nL the increasing amount of 2-fluorotoluene results in improved peak definition. It is significant to note in FIG. 5(b) that the 2-fluorotoluene peak B becomes shifted to later retention times as sample size increases. The chromatogram of FIG. 5(c) shows in trace 62 a condition in which no backflushing is used for the sake of comparison. For traces 62–68 only 80 parts-per-million of 2-fluorotoluene was present in the toulene solvent. Trace 64 represents a single backflushing operation in which the 2-fluorotoluene peak remains obscured. Trace 66 represents a second backflushing operation in which the peak B of the 2-fluorotoluene begins to be observable. Finally, with three backflushes shown by trace 68, the toluene peak A with 2-fluorotoluene peak B become clearly visible and compares favorably to the trace for equal concentration shown in FIG. 5(a).

The previously described operation of gas chromatography systems 10 is provided through the control of computer 42 which actuates valve assembly 38 at the appropriate time after the sample is injected into the column 32. For repeated analysis of a relatively constant sample, the backflush time can be set to a predetermined value allowing the system to be automated for process control or process statistics gathering operation without operator intervention.

As is further evident from the above description, the backflush and retrapping mode of operation of this system does not make use of valve assembly 40 whose function will be described subsequently. Accordingly, in an embodiment of this invention which provides only the backflushing and retrap mode, valve assembly 40 and the conduit to which it is connected can be eliminated entirely.

Again with reference to FIG. 1 the mode of operation referred to as "backflushing" (without retrapping and reinjection) can be described. This mode of operation begins with the normal process of allowing a sample to collect in cooling chamber 16 and is, thereafter, injected into column 32, by causing fluid to flow through both of these elements in a left-to-right hand direction with reference to FIG. 1. To cause a backflushing of the column 32, valve 38 remains closed whereas valve 40 is opened while pump 30 is operated. The vacuum generated by vacuum pump 30 continues to allow the normal flow direction of fluid to occur through capillary tube 14. However, the flow through column 32 is in a reverse direction, i.e. from right-to-left. The purpose of such reverse flow is to expedite gas chromatography procedures in conditions where higher boiling point constituents of the mixture which may not be of interest in a particular evaluation process can be eliminated from the column without having to await their elution from column 32.

Figure 6A:
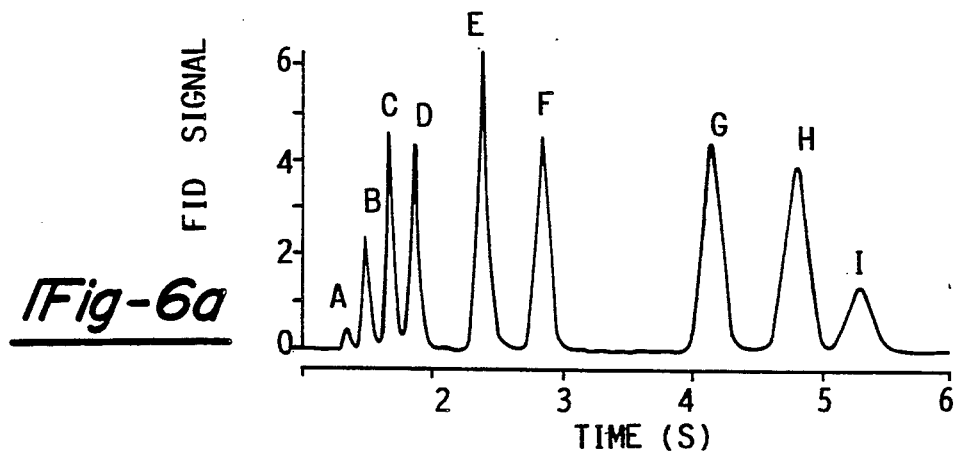
FIGS. 6(a) through 6(d) show, in FIG. 6(a) a partial chromatogram of a mixture of interest, in FIG. 6(b) the complete chromatogram of the mixture of FIG. 6(a) showing peaks associated with higher boiling point components, in FIG. 6(c), the chromatogram of the test mixture with backflush initiated, and at FIG. 6(d) a series of chromatograms of successive samples with backflushing operation.
Figure 6B:
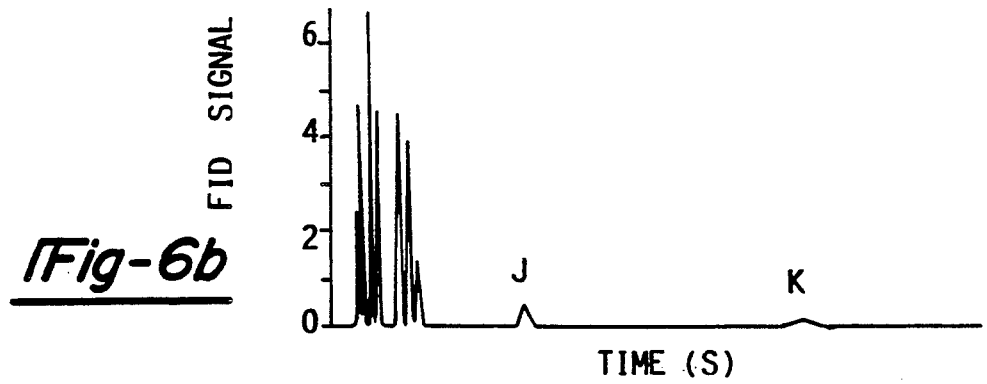

The backflushing operation is graphically depicted in FIG. 6(a) through 6(d). FIG. 6(a) is a chromatogram plotted on an expanded time scale showing a nine component mixture of relatively volatile components. These peaks are arbitrarily lettered A through I in FIG. 6(a). FIG. 6(b) shows the same chromatogram on compressed time scale. As is shown in FIG. 6(b) higher boiling point residues elute much after the nine components mentioned previously and produce the peaks identified as peaks J and K. These peaks correspond with an elution time of 12 and 28 seconds, respectively. As mentioned previously, there are numerous procedures in which the peaks J and K would not be of interest of awaiting their elution imposes a limitation in the speed at which the chromatography procedure can be carried out. It would be unacceptable to simply reinject another sample after peaks A-I have eluted without backflushing, since peaks J and K would become overlaid on subsequent chromatograms giving rise to distortion of the output.

Figure 6C:
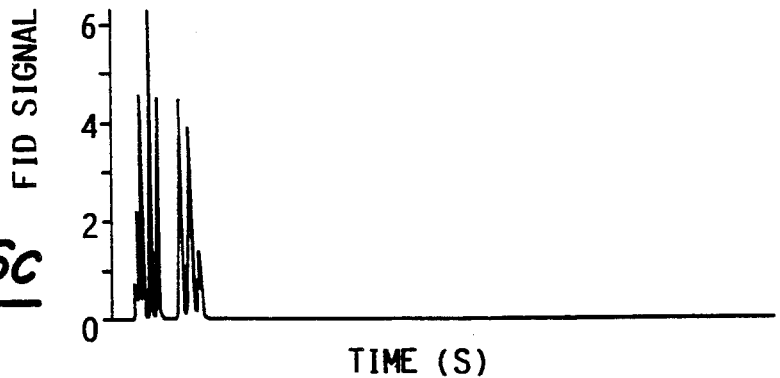
Figure 6D:
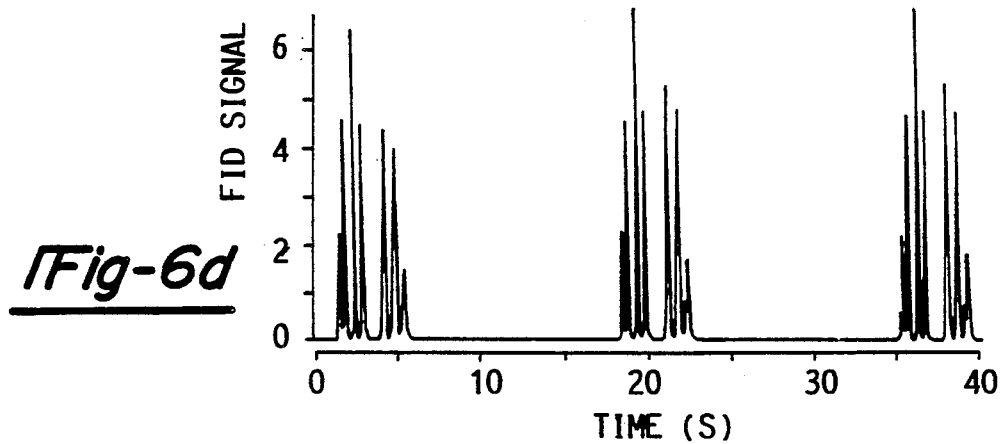

The chromatogram shown in FIG. 6(c) illustrates operation when a five second backflush operation is initiated six seconds after sample injection. The higher boiling point components J and K are completely removed. FIG. 6(d) is three repetitive chromatograms of the same mixture shown in FIG. 6(a). For this chromatogram, a five second backflush was initiated six seconds after each sample injection. As is evident from FIG. 6(d), three complete chromatograms can be generated in 40 seconds which is only slightly longer than necessary in order to generate one complete chromatogram with the higher boiling point components being eluted as shown in FIG. 6(b).

While column 32 is being backflushed by opening valve 40, the flow through metal capillary tube 14 is i its "normal" flow direction. Accordingly, while backflushing is occurring, cooling of chamber 16 allows the next sample to be collected and thermally focused.

The backflushing operation according to this invention is provided without the necessity of applying a high pressure gas source to drive the flow from the exit end of the column 32. Rather, the vacuum generated by pump 30 acting against atmospheric pressure is the sole pressure for driving feasible using long column lengths. However, in accordance with this invention in which columns of less than ten meters and preferably about two meters are used, such vacuum backflushing operates well in relatively small backflush times. Since the backflush time is a function of the square of the column length, systems having long column lengths are unsuited for vacuum driven backflushing in accordance with the above description of this invention. For backflushing operation without retrapping and reinjection, valve 38 and the associated conduit 34 can be eliminated entirely.

While the above description constitutes the preferred embodiments of the present invention, it will be appreciated that the invention is susceptible of modification, variation and change without departing from the proper scope and fair meaning of the accompanying claims.

We claim:

1. A method of conducting a gas chromatography experiment comprising the steps of:
   providing a sample source and a carrier gas source,
   providing a thermal focusing chamber with means for cooling a sample to collect it and for heating said sample to vaporize it,
   providing a gas chromatography separation column,
   providing conduit means communicating with said sources, said chamber and said column,
   providing a vacuum pump connected with said conduit means at a point between said sources and said thermal focusing chamber,
   providing a detector for sensing the presence of components of said sample as they are eluted from said column,
   introducing said sample into said chamber while said chamber is cooled to collect said sample, said sample including components which elute from said column at or before a threshold separation time and components which would elute after said threshold time,
   vaporizing said sample and injecting said sample into said column,
   causing said vacuum pump to draw said sample and said carrier gas from said column at said threshold time causing said components which would elute after said preselected time to be drawn into said chamber, cooling said chamber such that said components which would elute after said preselected time recollect in said chamber.

2. A method of conducting a gas chromatography experiment according to claim 1 wherein said threshold separation time is a time within the time period at which a high magnitude long duration peak is observed by said detector whereby at least some portion of the components generating said peak has eluted from said column and is, therefore, separated from non-eluted components which are returned to said chamber, allowing the presence of other components which produce peaks superimposed upon said high magnitude peak to be detected.

3. A method of conducting a gas chromatography experiment according to claim 2 wherein said steps of vaporizing said sample, causing said vacuum pump to draw said sample, and cooling said chamber are repeated more than once to reduce the concentration of said high magnitude long duration peak generating component.

4. A gas chromatography system comprising:
a sample source,
a carrier gas source,
a thermal focusing chamber having means for cooling said chamber for collecting a sample,
a chromatography separation column having a length of equal to or less than 10 meters,
first conduit means for conducting a sample and a carrier gas from said sources through said thermal focusing chamber and thereafter to said column,
a heater circuit for rapidly heating said first conduit means within said thermal focusing chamber for vaporizing said sample,
a vacuum pump,
second conduit means communicating said pump with said first conduit means at a point between said chamber and said column,
first valve means for controlling flow of fluids through said second conduit means,
third conduit means communicating said pump with said first conduit means at a point between said chamber and said sample and carrier gas source,
second valve means for controlling flow of fluids through said third conduit means,
control means for closing both said first and second valve means allowing fluid flow from said sources through said chamber and into said column in an initial forward direction, or opening said first valve means for causing fluid flow in a reverse direction through said column for backflushing said column, or opening said second valve means for causing fluid flow in a reverse direction through both said column and said chamber causing components of said sample which have not eluted from said column to be returned to said chamber for recollection, and
a detector for sensing the presence of components of said sample which have eluted from said column.

5. A gas chromatography system according to claim 4 wherein said control means causes said first valve means to open during separation of a sample in said column at a time wherein not all of the components of said sample have eluted from said column thereby backflushing and venting non-eluted components.

6. A gas chromatography system according to claim 5 wherein said thermal focusing chamber is cooled to collect said sample while said first valve means is open for said backflushing and venting.

7. A gas chromatography system according to claim 4 wherein said control means opens said second valve means when not all of the components of said sample have eluted from said column and wherein said thermal focusing chamber is cooled thereby recollecting non-eluted components.

8. A gas chromatography system according to claim 7 wherein said control means closes said second valve means to cause said non-eluted components to be reinjected into said column.

9. A gas chromatography system according to claim 4, wherein said column has a length of approximately 2 meters.

10. A gas chromatography system comprising:
a sample source,
a carrier source,
a thermal focusing chamber, having means for cooling said chamber for collecting a sample,
a chromatography separation column having a length of equal to or less than 10 meters,
first conduit means for conducting said sample and a carrier gas from said sources through said thermal focusing chamber and thereafter to said column,
a heater circuit for rapidly heating said first conduit means within said thermal focusing chamber for vaporizing said sample,
a vacuum pump,
second conduit means communicating said pump with said first conduit means at a point between said chamber and said sources,
valve means for controlling the flow of fluids through said second conduit means,
control means for operating said valve means such that, in an initial flow condition, said valve means is closed allowing said sample and said carrier gas to flow through said first conduit means and into the entrance end of said column for separation, and in a backflush and retrap condition, opens said valve means causing components of said sample which have not eluted from said column to be returned to said chamber for recollection and reinjection into said column, and
a detector for sensing the presence of components of said sample which have eluted from said column.

11. A gas chromatography system according to claim 10 wherein said control means opens said valve means when not all of the components of said sample have eluted from said column and wherein said thermal focusing chamber is cooled thereby recollecting non-eluted components.

12. A gas chromatography system according to claim 10 wherein said control means closes said valve means to cause said components returned to said chamber to be reinjected into said column.

13. A gas chromatography system according to claim 10 wherein said column has a length of approximately 2 meters.

* * * * *

UNITED STATES PATENT AND TRADEMARK OFFICE
CERTIFICATE OF CORRECTION

PATENT NO. : 5,096,471

DATED : March 17, 1992

INVENTOR(S) : Richard Sacks et al.

It is certified that error appears in the above-identified patent and that said Letters Patent is hereby corrected as shown below:

On the title page under "inventors" delete "Christine Rankin".

Signed and Sealed this

Fourteenth Day of December, 1993

Attest:

BRUCE LEHMAN

Attesting Officer     Commissioner of Patents and Trademarks